United States Patent [19]

Perkins

[11] Patent Number: 5,038,770
[45] Date of Patent: Aug. 13, 1991

[54] FAIL-SAFE SYSTEMS FOR RESPIRATING GAS DELIVERY DEVICES

[76] Inventor: Warren E. Perkins, 9960 S. Ocean Dr., #1901, Jensen Beach, Fla. 34957

[21] Appl. No.: 305,766

[22] Filed: Feb. 3, 1989

[51] Int. Cl.⁵ ............................................. A61M 16/00
[52] U.S. Cl. ........................ 128/204.18; 128/204.21; 128/204.23; 128/205.24; 128/204.26
[58] Field of Search ................... 128/204.18, 204.21, 128/204.23, 204.26, 205.16, 205.18, 205.24, 205.23, 202.22, 204.24

[56] References Cited

U.S. PATENT DOCUMENTS

| | | | |
|---|---|---|---|
| 3,292,617 | 12/1966 | McDonough | 128/205.16 |
| 4,203,434 | 5/1980 | Brooks | 128/205.23 |
| 4,457,303 | 7/1984 | Durkan | 128/204.24 |
| 4,462,398 | 7/1984 | Durkan et al. | 128/204.23 |
| 4,498,471 | 2/1985 | Kranz et al. | 128/204.26 |
| 4,705,034 | 11/1987 | Perkins | 128/204.26 |
| 4,706,664 | 11/1987 | Snook et al. | 128/204.23 |
| 4,836,198 | 6/1989 | Gates | 128/205.18 |
| 4,873,971 | 10/1989 | Perkins | 128/204.23 |

Primary Examiner—Aaron J. Lewis
Attorney, Agent, or Firm—Roland H. Shubert

[57] ABSTRACT

A fail-safe system for use with pulse dose respirating gas delivery devices provides a continuous, metered flow of oxygen to the patient in the event that the delivery device malfunctions or suffers a power failure. The system includes a piston resiliently biased toward one end of a cylinder and having provision for applying the force of pressurized respirating gas on the piston in opposition to the biasing force and in synchronization with doses of respirating gas produced by the delivery device and to remove that force in coordination with the delivery of a gas dose to the patient. The piston movement is arranged to actuate valve means opening a path for the continuous flow of oxygen to the patient in the event that successive gas doses are not delivered to the patient within a predetermined length of time.

32 Claims, 4 Drawing Sheets

FAIL-SAFE SYSTEMS FOR RESPIRATING GAS DELIVERY DEVICES

BACKGROUND OF THE INVENTION

1. Field of the Invention:

This invention relates generally to fail-safe systems for respirating gas delivery devices which provide pulsed doses of respirating gas to a patient.

More specifically, this invention relates to fail-safe systems which ensure a continuing flow of respirating gas to a patient in the event that a pulse-dose respirating gas delivery system fails to operate properly.

2. Description of Related Art:

It has long been conventional practice to administer supplemental oxygen to patients suffering from chronic obstructive pulmonary diseases and other respiratory ailments. Devices commonly used for oxygen administration deliver a constant flow of oxygen at a fixed rate to a mask placed over the patient's nose and mouth or through a cannula which terminates in nares inserted into the patient's nostrils.

Constant flow devices waste a substantial portion of the oxygen because that oxygen provided during the exhalation and pause phases of the patient's respiratory cycle cannot be used. Consequently, devices have been developed to conserve oxygen by regulating the oxygen flow, turning it on and off, in synchronization with the respiratory cycle. Typically these devices operate by sensing the beginning of an inspiration and delivering pulses or doses of oxygen at a relatively high rate beginning at the start of inspiration but lasting for only a small part of the inspiration period.

The sensors and control circuitry for such devices are ordinarily powered by electricity and require a current source such as a battery. Also, the valves used to control oxygen flow are usually electrically operated solenoid valves. Delivery of oxygen doses will cease in the case of malfunction of the sensor or the control circuitry or the failure of the power source. A delivery failure can have serious adverse effects upon a patient and may even become life-threatening. Consequently, pulse dose oxygen delivery systems typically have some means for switching to a continuous delivery mode upon need.

Pulse dose oxygen systems known in the prior art fall generally into two types; one type employing rate-time metering and the other type employing volumetric metering. An example of a volumetric metering system is shown by appliant's U.S. Pat. No. 4,705,034. The demand oxygen controller developed by Dr. Gerald Durkan, represented for example by his U.S. Pat. Nos. 4,457,303 and 4,462,398, is of the rate-time metering type. It employs in its commercial embodiment a manually operated selector switch which changes the gas delivery between a pulsed and a continuous flow mode. The continuous flow mode requires no electrical power.

Another example of a pulse dose oxygen delivery system employing rate-time metering is the Puritan-Bennett device described in U.S. Pat. No. 4,706,664. That apparatus is designed to revert to conventional, continuous flow operation upon a power failure or circuit malfunction. Reversion to continuous flow operation is accomplished by mechanically biasing an electrically operated solenoid valve so that it will move to an open position whenever the solenoid is de-energized. That arrangement requires the solenoid to have sufficient power to overcome the mechanical biasing force as well as to change the valve position. The solenoid must also remain energized so long as the valve is in the closed, or flow blocking, position.

The back-up systems of the prior art, allowing for a change from pulse dose delivery of oxygen to a continuous delivery mode in case of malfunction or power failure, all have practical disadvantages. The Durkan system requires that the patient recognize the malfunction and physically change the position of a selector switch. The Puritan-Bennett system, while functioning automatically, greatly increases the power consumption of the unit because of the need to maintain a mechanically biased solenoid valve in an energized state.

SUMMARY OF THE INVENTION

This invention provides a method and means for establishing emergency, or fail-safe, flow to an oxygen patient being supplied by an intermittent flow system whereby a continuous flow of oxygen or other respirating gas is delivered to the patient in the event that the flow system stops delivering doses for any reason except for depletion of the supply gas. It may be used with either rate-time metering systems or volumetric metering systems.

The fail-safe device of this invention includes a movable piston arranged within a cylinder and resiliently biased by a spring or other suitable means toward one end of the cylinder. A force exerted by respirating gas is periodically supplied to the cylinder end opposite the biasing means in synchronization with the doses of respirating gas produced by the system for delivery to a patient. The pressure of the supplied gas is sufficiently high to cause the piston to overcome the biasing force and move within the cylinder. Means are also provided to relieve the force exerted by the gas pressure upon the cylinder in coordination with the system deliveries of gas doses to the patient. A valving means is actuated by movement of the piston toward its extreme position allowing continuous metered flow of respirating gas from the gas source to the patient. The biasing force on the piston is adjusted relative to the applied force of the respirating gas and the rate of force application to the cylinder is set so that a predetermined length of time is required for the piston to move to its extreme position and actuate the valving means. Each time a dose is delivered to the patient the system tends to be reset, starting anew that predetermined length of time for actuation of the valving means.

Hence, it is an object of this invention to provide a method and means to automatically establish a continuous metered flow of respirating gas to a patient in the event that a pulse dose delivery system malfunctions or incurs a power failure.

Another object of this invention is to provide a fail-safe system useful with pulse dose gas delivery devices of either the volumetric metering or rate-time metering type.

Other objects of the invention will be apparent from the following description of certain embodiments of the invention.

BRIEF DESCRIPTION OF THE DRAWING

Specific embodiments of the invention are illustrated in the drawing in which.

DETAILED DESCRIPTION OF THE INVENTION

The fail-safe system of this invention may be used with both rate-time and volumetric pulse-dose gas delivery devices. It may be incorporated as an integral part of either type of gas delivery device or it may be used as an add-on accessory to existing units.

Figure 1:
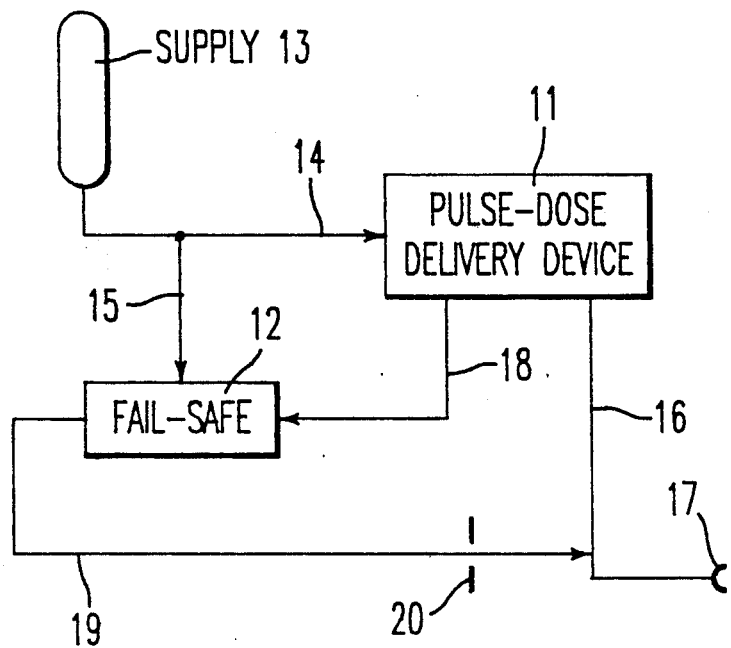
FIG. 1 is a block diagram illustrating the components of a pulse dose gas delivery system including the fail-safe system of this invention.

FIG. 1 broadly illustrates the invention in block diagram form in which a pulse-dose gas delivery device 11 is interconnected with fail-safe system 12 and pressure regulated respirating gas supply 13. Gas delivery device 11 may be of the rate-time type such as those of Durkan and Puritan-Bennett referred to earlier or it may be of the volumetric type described in applicant's prior U.S. Pat. No. 4,705,034, the disclosure of which is incorporated by reference herein.

Respirating gas from supply 13, typically oxygen, is furnished to the delivery device by way of conduit means 14 and to fail-safe system 12 through conduit 15. The pulse-dose delivery device typically includes means to sense the start of an inspiration and then to immediately deliver a measured gas dose to a patient by way of cannula 16. Cannula 16 may appropriately terminate in nares 17 positioned in the nostrils of the patient. Supply 13 may be a cylinder containing oxygen at high pressure or a Dewar flask holding liquid oxygen or, in the case of stationary systems in a hospital or like environment, may be an oxygen line. An appropriate connection 18 is provided between the dose delivery device and the fail-safe system so as to apply and relieve a force upon the system in synchronization with the patient's respiratory cycle. In the event that the time interval between successive doses delivered by device 11 exceeds a predetermined length, the fail-safe system 12 operates to deliver a continuous stream of respirating gas at a controlled pressure above atmospheric from supply 13 and conduit 15 through conduit 19, which joins with cannula 16, for breathing by the patient. A rate setting orifice 20 is placed either in conduit 19 as shown or in conduit 15 to regulate the flow of gas to the patient.

Figure 2:
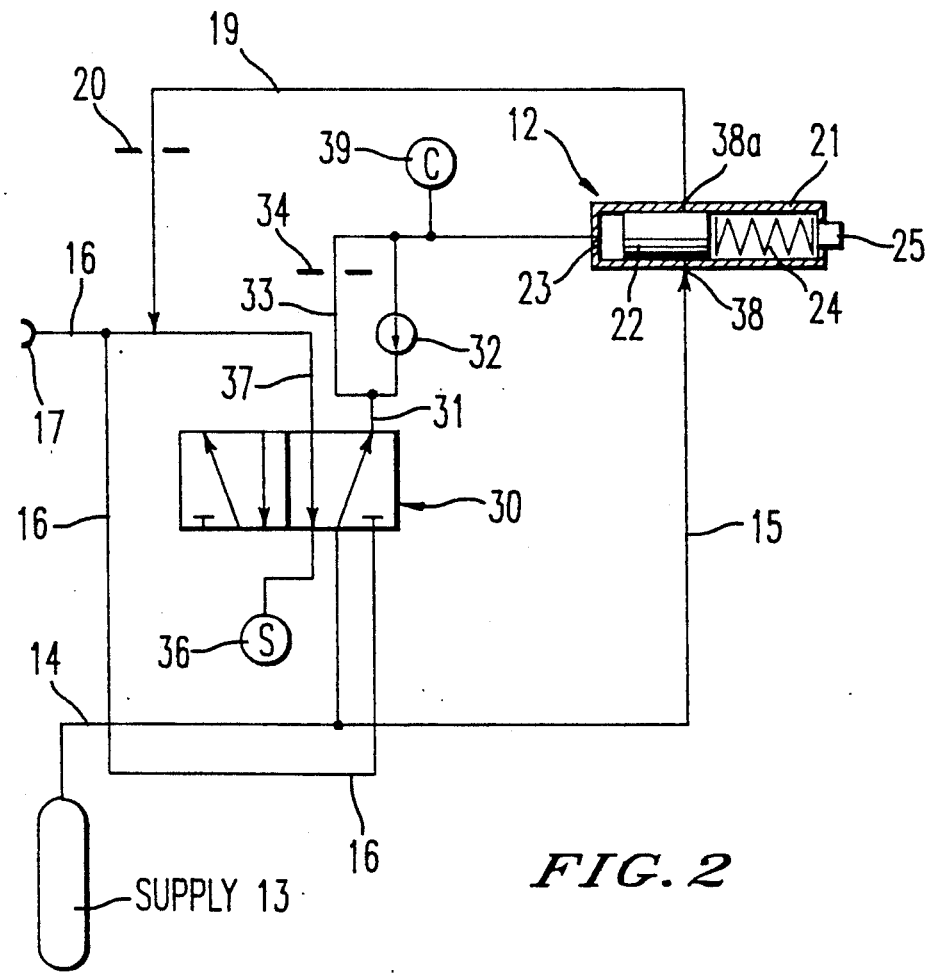
FIG. 2 is a generally schematic drawing in partial cross-section showing the fail-safe system incorporated with a gas delivery system employing rate-time metering.

FIG. 2 shows a specific embodiment of the invention for dosing systems using rate-time metering. This Figure shows only the gas flow paths within the system and does not show the complete control circuit which may be, for example, that described in the Durkan U.S. Pat. No. 4,457,303. In this embodiment, fail-safe system 12 comprises a cylinder 21 having a piston 22 disposed therein. The piston 22 is biased toward end 23 of cylinder 21 by a force applied on the piston by a resilient biasing means such as spring 24. A vent 25 is provided at the other cylinder end to allow free passage of gas into and out of cylinder 21 as piston 22 moves back and forth.

Valve 30 is a four-way, single solenoid, spring return, five port valve or its functional equivalent which is a part of the pulse-dose delivery device and operates in response to signals produced by the control circuit of that device. In the valve position illustrated, which is the unpowered or normal position, a sensor 36 is in fluid communication with nares 17 through cannula 16 and line 37 while oxygen from source 13 is directed along a path through conduit 14 and through valve 30 to line 31 having check valve 32 positioned therein. Check valve 32 is arranged so as to allow flow only in the direction of the arrow. A by-pass loop 33 is arranged to allow gas flow around check valve 32 and into cylinder 21 at a low bleed rate set by bleed orifice 34. Gas flowing into cylinder 21 slowly pushes piston 22 to the right overcoming the opposing force applied by spring 24. Conduit 15 communicates between source 13, by way of line 14, and a valve port 38 in the wall of cylinder 21. Another valve port 38a is provided in the cylinder wall opposite port 38. Valve ports 38 and 38a are normally closed or blocked by piston 22.

Operation of the system is as follows. Sensor 36 may be any appropriate pneumatic/electrical sensing apparatus capable of sensing the beginning of a patient's inhalation. Upon detecting the onset of an inhalation, sensor 36 produces a signal which is transmitted to and processed by the control circuit of the device (not shown). In response to an inhalation signal, the control circuit powers a valve actuator (not shown) causing valve 30 to move to its powered position. In that other powered position the gas flow paths through the valve are as diagrammed on the left half of the valve. That is, line 31 is connected through valve 30 to cannula 16; line 14 is connected through valve 30 to cannula 16; and sensor 36 is isolated. The valve remains in this other position for a length of time set by the size of the gas dose being administered to the patient. The valve actuator or solenoid is then unpowered and the valve returns to its normal unpowered position. Normally the time during which valve 30 is powered is set to be considerably less than the duration of a normal inhalation thus causing the gas dose to be administered during the early stages of the inhalation.

Each time the system delivers a pulse dose the pressure in cylinder 21 is relieved by gas flow from the cylinder through check valve 32, four-way valve 30, and the cannula 16. That release of pressure from cylinder 21 causes piston 22 to travel to the left cylinder end under pressure from spring 24. Now if for any reason the pulse dose delivery device stops delivering doses, then valve 30 in its unpowered position allows a bleed flow of gas to continue passing to cylinder 21 through line 31. At some point, piston 22 will be forced so far to the right as to uncover valve ports 38 and 38a. That will then allow gas to flow continuously from source 13 through cylinder 21 and line 19 to cannula 16 and thence to the patient. Rate of gas flow is governed by flow controlling orifice 20.

The length of time between delivery of the last dose and the establishment of emergency continuous gas flow to the patient is set by adjustment of the size of bleed orifice 34, the length of travel of piston 22 before it uncovers valve ports 38 and 38a, and the strength of spring 24. If normal operation of the device resumes, then the fail-safe device 12 is automatically reset by release of the pressure within the cylinder allowing piston 22 to move to the left and again cover the valve ports.

Operation of the fail-safe device will tend to marginally increase the dose size as the patient breathes more slowly. This effect is due to the volume of gas within cylinder 21 which is delivered to the patient along with the normal dose. The effect of increasing the dose size as the respiration rate slows can be further enhanced by providing a capacitance chamber 39 in parallel with cylinder 21. The size of capacitance 39 also influences the time interval between delivery of the last dose and establishment of continuous gas flow to the patient. The valve arrangement shown protects sensor 36 from the pressure surge of delivered gas pulses. For systems not requiring protection of the sensor, a four-way, four-port reversing valve may be substituted for the five-ported valve shown.

Figure 3:
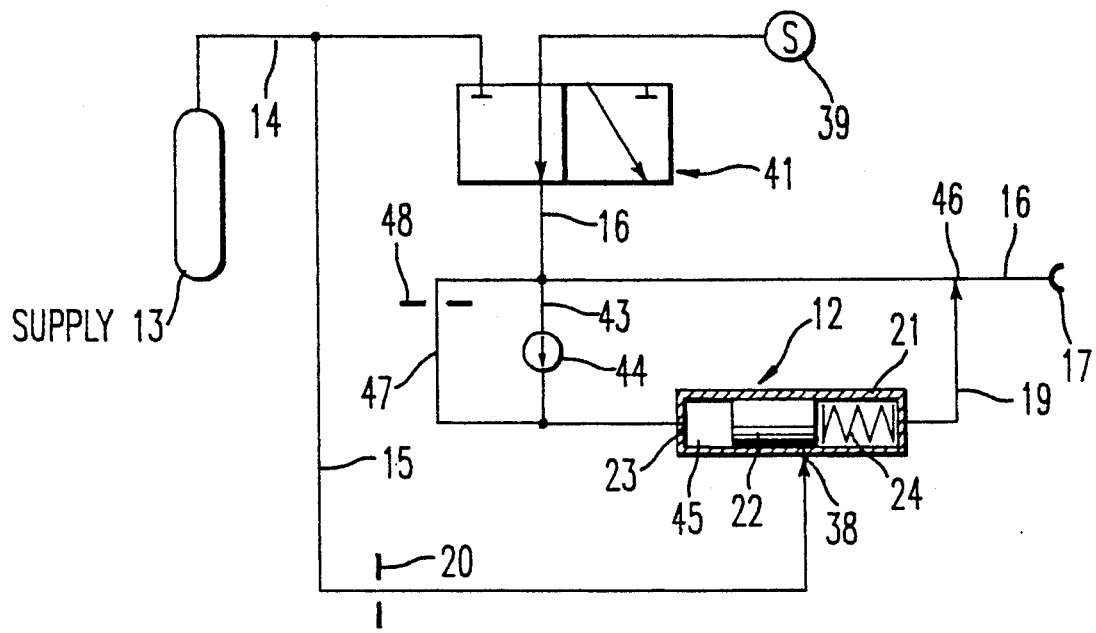
FIG. 3 is a generally schematic drawing in partial cross-section depicting the fail-safe system employed with a rate-time metering device which uses a 3-way valve.

Turning now to FIG. 3, there is shown another embodiment of the fail-safe system of this invention. This embodiment provides for establishing emergency or fail-safe flow to a patient being supplied by a rate-metered, intermittent flow system which uses a three-way valve to temporarily connect the supply to the cannula during the pulse-dose delivery time interval.

As with the embodiment of FIG. 2, there is provided a supply of oxygen or other respirating gas 13 at a controlled pressure above atmospheric. Line 14 connects the supply 13 with one side of a flow control valve 41 while a branch line 15 leads to a valve port 38 in a side cylinder wall of fail-safe unit 12. The fail-safe unit 12 is similar to that one depicted in FIG. 2 and comprises a cylinder 21 having a piston 22 disposed therein. Piston 22 is biased toward cylinder end 23 by the force of biasing spring 24. Unlike the embodiment of FIG. 2, the other cylinder end is not vented but instead connects directly to line 19 so as to provide communication between the interior of cylinder 21 and cannula 16. A rate setting orifice 20 to govern the gas flow to the patient when the system is in its continuous flow mode is located in line 15 rather than in line 19 for reasons which will later become evident.

This embodiment of the invention operates in the following manner. Valve 41 is a three-way, single solenoid, spring return valve, or its functional equivalent, shown in its normal or unpowered position. In this valve position, sensor 39 communicates through the valve and cannula 16 directly with the open ends of nares 17. The sensor 39, upon detecting a pressure drop indicative of the start of an inhalation, produces a signal which is transmitted to appropriate control circuitry (not shown). In response to an inhalation signal, the control circuit powers valve 41 causing it to move to its other position diagrammed on the right half of the valve drawing. The valve 41 in its other, or powered, position isolates sensor 39 from the system and connects supply line 14 with cannula 16. That connection is maintained for a predetermined length of time sufficient for the desired gas dose to be delivered through the cannula and nares to the patient. Thereafter, power is removed from valve 41 and it returns to its normal position.

Whenever a pulse of oxygen or other gas is delivered to the patient via the cannula 16 a small quantity of the gas pulse is also directed into line 43 leading through a check valve 44 into space 45 within cylinder 21. Space 45 acts as a capacitance chamber to store the gas against the force of bias spring 24 and a gas pressure which during delivery of a gas dose is momentarily less than cannula pressure because of the venturi effect of the gas dose rushing over the connection port 46 at the juncture of line 19 and cannula 16. The rate setting orifice 20 is preferably located in line 15 rather than in line 19 so as to maximize the venturi effect.

Pressure exerted on the gas in space 45 by spring 24 acting through piston 22 causes a slow bleed flow back to the cannula through by-pass line 47 and bleed orifice 48 during non-pulse times. As the gas in space 45 is bled off, piston 22 progressively moves leftward toward the end 23 of the cylinder. So long as gas pulses continue to be delivered to the patient, the gas within space 45 is renewed, repeatedly pushing piston 22 to the right with each delivered dose. If sufficient time elapses between gas doses, the gas within space 45 will be depleted allowing piston 22 to move to the far left and approach the cylinder end. Upon approaching the cylinder end, piston 22 uncovers port 38 in the side wall of cylinder 21 thereby starting an emergency fail-safe flow of gas to the patient. Uncovering of port 38 allows gas to continuously flow from supply 13, through lines 14 and 15 and passing through port 38 to line 19 and cannula 16, for delivery to the patient. The rate of gas flow is, of course, governed by rate setting orifice 20. The length of time between delivery of the last gas pulse and initiation of emergency flow may be varied by changing either the volume of space 45 within cylinder 21, the size of bleed orifice 48, or the force of spring 24. The system will automatically revert to intermittent flow if delivery of gas pulses resumes.

Figure 4:
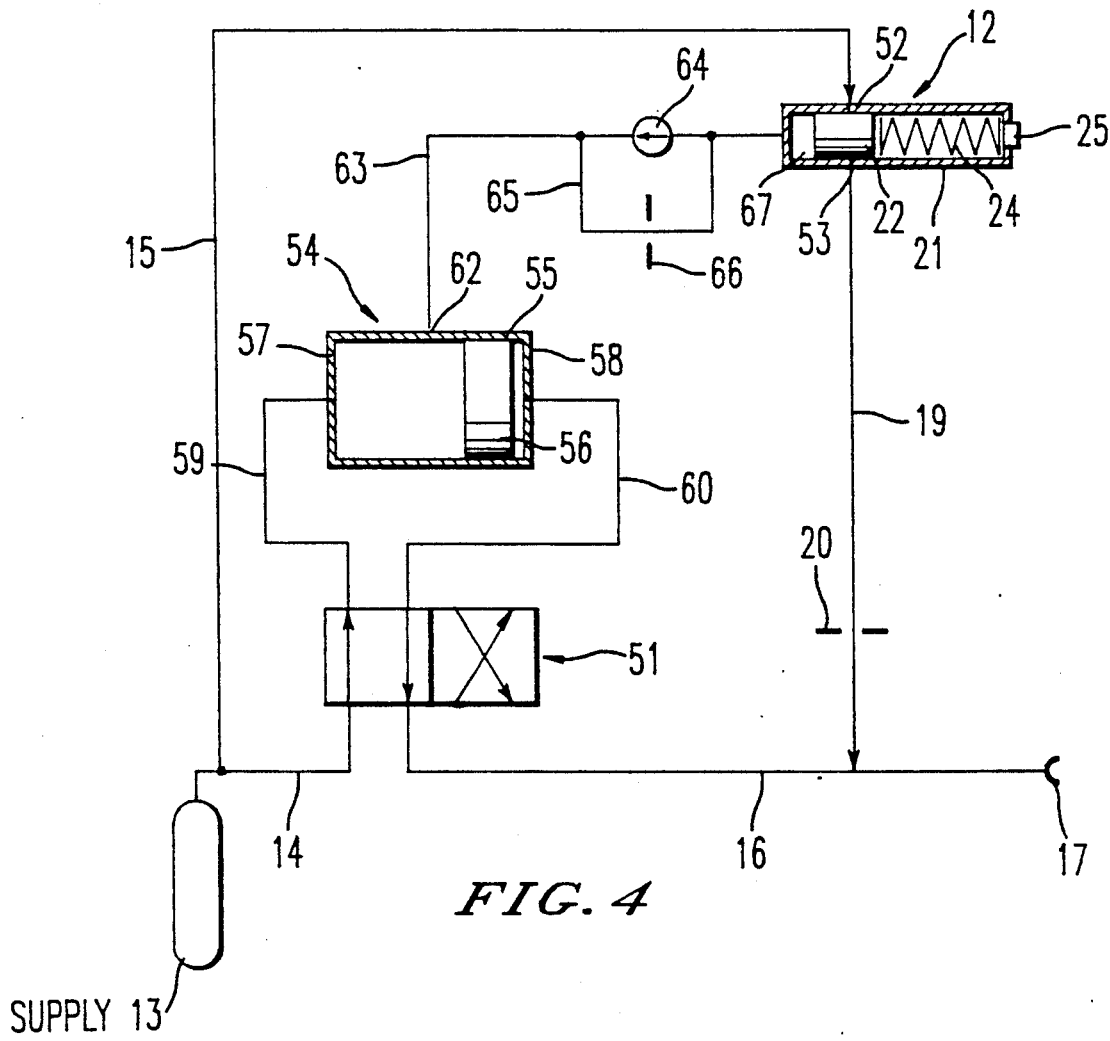
FIG. 4 is a generally schematic drawing in partial cross-section showing the fail-safe system used with a double-acting, volumetric metering-type dispenser.

FIG. 4 shows the fail-safe device of this invention arranged for use with a double-acting volumetric displacer of the type described and claimed in applicant's prior U.S. Pat. No. 4,705,034. In this arrangement there is provided as before an oxygen supply 13 having line 14 connecting the supply to one port of a flow control valve 51. A branch line 15 leads between line 14 and a port 52 in the wall of cylinder 21 of fail-safe device 12. Volumetric displacer 54 comprises a closed cylinder 55 having a piston 56 disposed therein. Piston 56 is free to reciprocate back and forth from one cylinder end 57 to the other cylinder end 58. A conduit 59 extends through cylinder end 57 to the interior of cylinder 55 and communicates with a port of valve 51. A similiar conduit 60 extends through cylinder end 58 and communicates with a second port of valve 51.

Following the operation of the device through one complete cycle, valve 51 in the position shown provides a direct connection between oxygen supply 13 and the interior of cylinder 55 by way of line 14, valve 51 and line 59. The other end of cylinder 55 is in open communication with the cannula 16 by way of line 60 and valve 51 for the delivery of a dose of oxygen to a patient through nares 17. Because the oxygen supplied through line 59 is at an elevated pressure, it forces piston 56 to the end 58 of cylinder 55 pushing out the oxygen in that end of the cylinder through line 60. When the piston reaches the end 58 of the cylinder, it stops and the free space, or cylinder volume, to the left of the piston is filled with oxygen at a pressure equal to the supply pressure.

A port 62 is provided in the wall of cylinder 55 at a point midway between its ends. Conduit means 63 connects port 62 to the interior of cylinder 21 of fail-safe device 12 as shown. A check valve 64 is placed in conduit 63 and allows flow only in the direction of the arrow. There is also provided a by-pass line 65 around check valve 64; the flow in by-pass 65 being restricted by bleed orifice 66. Now when displacer piston 56 passes the midpoint of cylinder 55 and nears end 58, port 62 is uncovered and exposed to oxygen at essentially supply pressure causing a flow of gas through bleed orifice 66 in the by-pass line 65 and into the interior of fail-safe cylinder 21. That gas flow causes piston 22 of the fail-safe device to move to the right against the resisting force of spring 24. Bleed flow through orifice 66 continues so long as displacer piston 56 is at the cylinder end.

Valve 51 is controlled by a sensor and control circuitry (not shown) which causes valve 51 to alternate between its two positions; the one shown and the one diagrammed on the right half of the valve drawing. Movement of the valve from its one position to its other position is synchronized with the start of an inhalation of the patient by the control circuit. As shown by the diagram, movement of valve 51 to its other position reverses the flow paths; connecting line 59 with the cannula 16 and connecting line 60 with the oxygen supply. Pressure on the left side of displacer piston 56 immediately drops as the gas rushes out of the cylinder and through cannula 16 and nares 17 to the patient. Piston 22 of fail-safe device 12 is also reset to the left because the check valve 64 allows for quick depressurization of space 67 within cylinder 21 exhausting to cannula 16 through displacer 54 and the valve 51. If the displacer piston 56 fails to cycle for any reason and remains at one end or the other of cylinder 62, then gas at supply pressure continues to bleed through orifice 66 and continues to push piston 22 to the right. Eventually, piston 22 moves far enough rightward to uncover ports 52 and 53 and open up an alternative metered path for a continuous flow of gas between the supply 13 and the cannula 16. If the displacer resumes normal operation, then the fail-safe device is depressurized allowing piston 22 to move leftward covering up ports 52 and 53 and so closing the alternative gas flow path. Rapid depressurization of the flow control device is ensured by providing a larger flow capacity through valve 64 and line 63 than is allowed through conduit 15. Valve 51 as shown in the drawing is a two-position, four-way reversing valve. However, other functionally equivalent valving such as the ganged arrangement of two three-way valves illustrated in U.S. Pat. No. 4,705,034 are also satisfactory.

Figure 5:
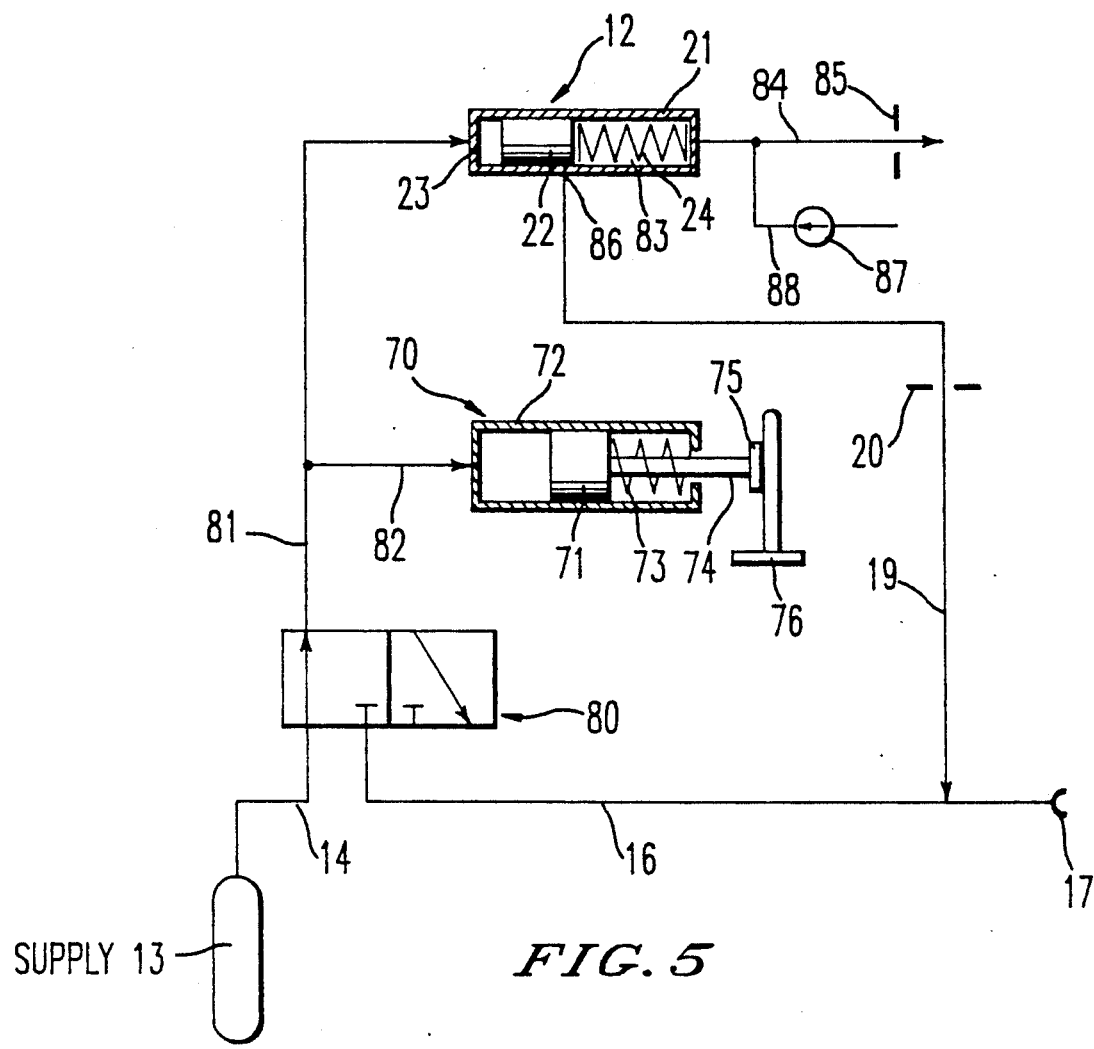
FIG. 5 is a generally schematic drawing in partial cross-section illustrating the fail-safe device arranged with a volumetric metering device.

FIG. 5 illustrates the fail-safe system of this invention used with another type of volumetric metering device. In this embodiment, volumetric metering displacer 70 comprises a piston 71 operating within a cylinder 72 while the flow control valve 80 is a three-way, two-position valve or its functional equivalent. Piston 71 operates against a spring 73 and has an attached piston rod 74 which limits the piston travel by engagement of rod end 75 with stop 76.

When the valve 80 is unpowered or in the position shown, oxygen from supply 13 is conveyed through the valve into conduit 81 which communicates with the interior of cylinder 21 of fail-safe device 12 through end 23 thereof. A branch line 82 supplies oxygen to metering displacer 70 applying pressure on the head of piston 71 and forcing it back against the pressure of the spring 73 until the piston rod end engages stop 76. At the same time, oxygen pressure on piston 22 of device 12 forces the piston toward the right against the force of spring 24 and against the pressure of air in the spring compartment 83. Pressure within compartment 83 is slowly relieved by flow of air through vent line 84 and flow restricting bleed orifice 85. Rightward movement of piston 22 continues so long as the valve 80 is in the position shown until finally the piston moves far enough to uncover port 86 in the wall of cylinder 21. At that time, a continuous flow of oxygen is established from source 13 through valve 80, line 81, fail-safe device 12 and line 19 to cannula 16 for delivery to a patient through nares 17. The flow rate is governed by flow regulating orifice 20.

Under the normal mode of operation of volumetric device 70, valve 80 would be caused to move to its other position upon detection of the start of an inhalation by the patient. The valve in its other position connects line 81 directly with cannula 16. Spring 73 then forces piston 71 to the left driving the oxygen before it through the connecting lines to the patient. At the same time, the force of spring 24 and the pressure of air within chamber 83 forces the fail-safe piston 22 to the left end of the cylinder. A check valve 87 in line 88 allows air to bypass bleed orifice 85 and refill chamber 83. After delivery of the oxygen dose contained in device 70 is complete, the system is arranged for valve 80 to revert to its first position and start the cycle anew. As will be appreciated, each time that valve 80 triggers a dose delivery, the fail-safe device 12 is reset. The time interval between delivery of the last gas dose and the establishment of continuous flow may be varied by changing the size of cylinder 21, by changing the flow rate allowed by bleed orifice 85 and by changing the force of spring 24.

The fail-safe system described in FIG. 5 works equally well with a metering device or displacer of the "blow-down" type. A blow-down metering device differs from the illustrated displacer 70 in that piston 71 is fixed and delivery of the oxygen dose to the patient is powered solely by expansion of the gas within the metering chamber.

Figure 6:
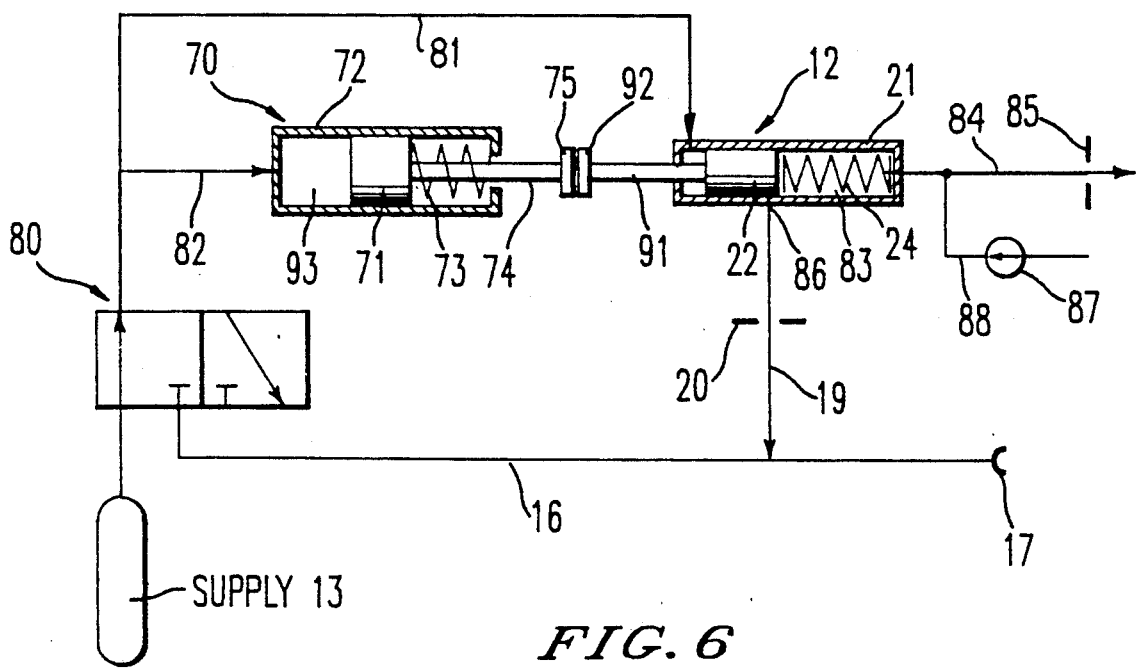
FIG. 6 is a generally schematic drawing in partial cross-section showing another embodiment of the fail-safe device used with a volumetric metering device and including provision for varying the dose size according to the respiration rate.

It is sometimes desirable to slightly vary the dose of oxygen delivered to a patient based upon the patient's respiration rate, increasing the volume of gas delivered per dose as the breathing rate slows. That result, as well as fail-safe delivery of oxygen in case of malfunction, can readily be accomplished without reliance on electrical circuitry in the manner shown in FIG. 6. Referring now to FIG. 6, there is shown an embodiment of the invention which may be considered to be a variant of that one described in relation to FIG. 5. Operation of the system of FIG. 6 is closely like that of FIG. 5 except for the mechanical, rather than pneumatic, interaction of displacer 70 and fail-safe unit 12. In this embodiment, fail-safe unit 12 functions in the manner of a dashpot having a piston rod 91 attached to piston 22 and extending through cylinder end 23 to terminate in rod end 92. Unit 12 is aligned with and positioned relative to displacer 70 so that the metering chamber piston 71 is limited in its travel by engagement of metering piston rod end 75 with fail-safe piston rod end 92.

When valve 80 is in its unpowered position as illustrated, metering chamber 93 of displacer 70 is filled and metering piston 71 is urged to the right by the pressure of the supplied oxygen. As piston 71 approaches its extreme position, further rightward movement is resisted by the force of the spring 24 and the pressure of air within spring compartment 83. The longer that valve 80 remains in its unpowered position the further to the right piston 22 is pushed and the larger will be the volume 93 of oxygen which will be delivered on the next dose delivery signal. If no dose delivery signals powering valve 80 to its other position are received for a given time, or if power is lost, the piston 22 will progressively move to the right until port 86 is opened. Opening port 86 establishes an orifice-metered continuous flow of oxygen to the patient.

Thus it can be seen that this embodiment varies the dose volume according to the respiration rate of the patient as well as providing a countinuous metered flow in the absence of signals calling for metered doses. If such signals are restarted and normal operation of the system resumed, the fail-safe unit 12 automatically resets itself for normal operation. Further, this embodiment of the invention will work equally well with an adjustably fixed, or blow-down, volume metering chamber where the chamber size adjustment is set by the position of rod 91.

Figure 7:
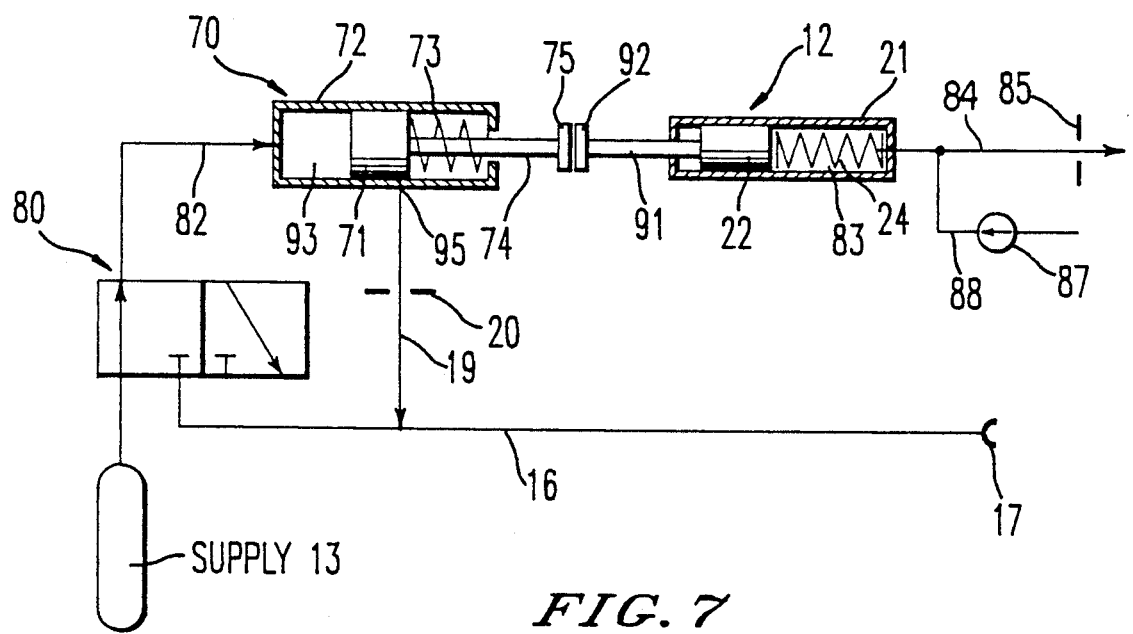
FIG. 7 is a generally schematic drawing in partial cross-section depicting a variation of the FIG. 6 embodiment.

FIG. 7 illustrates an alternative embodiment of the system of FIG. 6. In this embodiment, fail-safe unit 12 and displacer 70 are arranged as before with the metering chamber piston 71 limited in its travel by engagement of its piston rod end 75 with fail-safe piston rod end 89. As metering chamber 93 of displacer 70 is filled, piston 71 is urged to the right by the pressure of the supplied oxygen. After piston rod end 75 engages rod end 92, further rightward movement of piston 71 by a combination of forces including the resistance of spring 73, the resistance of spring 24 and the pressure of air within spring compartment 83. The longer that valve 80 remains in its unpowered position shown, the further to the right piston 71 is pushed. If no dose delivery signals powering valve 80 to its other position are received for a given time, or if power is lost, piston 71 will finally move far enough to uncover port 95 in the side wall of cylinder 72. That will then establish a continuous flow of oxygen from the source 13 through valve 80, conduit 82, displacer 70 and line 19 for delivery to the patient through the cannula and nares. Orifice 20 controls the flow rate. The fail-safe system will reset itself if normal operation of the displacer is resumed. As with the embodiment of FIG. 6, a further advantage is provided in that the dose volume is automatically varied with the respiration rate of the patient, the volume of gas delivered per dose increasing as the breathing rate of the patient slows.

While the invention has been particularly shown and described with reference to a number of preferred embodiments, it will be understood that various changes and alterations can be made without departing from the spirit and scope of the invention.

The embodiments of the invention in which an exclusive property is claimed are defined as follows:

I claim:

1. A fail-safe device for pulse dose respirating gas delivery systems, said device adapted to provide continuous gas flow to a patient in the event of system malfunction, comprising:

a movable piston disposed within a cylinder, said piston urged toward a first end of said cylinder by resilient biasing means;

means to periodically apply the force of pressurized respirating gas to the piston end opposite said biasing means in synchronization with doses of respirating gas produced by said system for delivery to a patient, the force produced by said pressurized respirating gas being sufficiently great to cause said piston to overcome the force of said biasing means and move toward the other cylinder end;

means to relieve the force of said gas upon said piston end in coordination with the cycling by the system in its delivery of gas doses to the patient thereby causing said piston to return toward said first cylinder end by action of said biasing means; and valve means actuated by movement of said piston to a specific position within said cylinder, the arrival of said piston at said specific position arranged to occur a predetermined length of time after delivery of a gas dose to the patient, said valve means when activated arranged to deliver a continuous metered stream of respirating gas to the patient.

2. The device of claim 1 wherein said means to relieve the force of gas upon said piston end acts after delivery of a gas dose to the patient.

3. The device of claim 1 wherein said means to relieve the force of gas upon said piston end acts upon delivery of a gas dose to the patient.

4. The device of claim 1 wherein said pulse dose gas delivery system is of the rate-time metering type.

5. The device of claim 1 wherein said pulse dose gas delivery system is of the volumetric metering type.

6. The device of claim 5 wherein said force of pressurized respirating gas is applied through a mechanical connection to said piston end.

7. The device of claim 5 wherein said force of pressurized respirating gas is pneumatically applied to said piston end.

8. A fail-safe device for pulse dose respirating gas delivery systems, said device adapted to provide continuous gas flow to a patient in the event of system malfunction, comprising:

a movable piston disposed within a cylinder, said piston urged toward a first end of said cylinder by resilient biasing means;

means to periodically supply respirating gas to the interior end of said cylinder opposite said biasing means in synchronization with doses of respirating gas produced by said system for delivery to a patient, the pressure of said supplied respirating gas being sufficiently high to cause said piston to overcome the force of said biasing means and to move toward the other cylinder end;

means to relieve the gas pressure within said cylinder in coordination with the cycling by the system in its delivery of gas doses to the patient thereby causing said piston to return toward said first cylinder end by action of said biasing means; and valve means actuated by movement of said piston to an extreme position opposite said first cylinder end, the arrival of said piston at said extreme position arranged to occur a predetermined length of time after delivery of a gas dose to the patient, said valve means when activated arranged to deliver a continuous metered stream of respirating gas to the patient.

9. The device of claim 8 wherein said pulse dose gas delivery system employs a two-position valve for rate-time metering, said valve in the first of said positions delivering a bleed stream of gas to the interior of said cylinder and, in the second of said positions, producing a pulse dose of gas for delivery to said patient while at the same time relieving the gas pressure within said cylinder 10. The device of claim 9 wherein said valve means comprise two ports in the wall of said cylinder, one of said ports communicating with the supply of said respirating gas and the other of said ports communicating with conduit means arranged for delivery of gas doses to the patient, said ports normally covered by said piston but uncovered upon arrival of said piston at said extreme position.

11. The device of claim 10 wherein said means to relieve the pressure within said cylinder includes a by-pass line around a check valve, said by-pass line having a bleed orifice limiting the rate of flow of gas to said cylinder and said check valve arranged to allow flow only from said cylinder.

12. The device of claim 11 including a capacitance adapted to increase the size of the gas dose delivered to the patient as the breathing rate of the patient decreases, said capacitance comprising a chamber arranged in parallel with said cylinder and located between said check valve and said cylinder, said chamber adapted to be filled through said bleed orifice and emptied through said check valve.

13. The device of claim 8 wherein said pulse dose gas delivery system is a double-acting volumetric displacer comprising a closed cylinder having a piston disposed therein, said piston free to move from one cylinder end to the other.

14. The device of claim 13 including conduit means communicating between a port located in the wall of said displacer cylinder at a point midway between its ends and the interior end of said fail-safe device cylinder, said conduit having a check valve located therein, said check valve allowing flow only toward said displacer cylinder port.

15. The device of claim 14 wherein a by-pass line is provided around said check valve, said by-pass line having a bleed orifice therein, said orifice adapted to allow a slow flow of gas around said check valve.

16. The device of claim 15 wherein said valve means comprise two ports in the wall of said cylinder, one of said ports communicating with the supply of said respirating gas and the other of said ports communicating with conduit means arranged for delivery of gas doses to the patient, said ports normally covered by said piston but uncovered upon arrival of said piston at said extreme position.

17. The device of claim 8 wherein said pulse dose gas delivery system is a volumetric metering displacer comprising a piston operating within a cylinder, said piston urged toward one end of the cylinder by resilient restoring means.

18. The device of claim 17 including a two-position flow control valve, said valve in its first position connecting the supply of said respirating gas through conduit means to the interior end of said displacer cylinder opposite said resilient restoring means and to the interior end of said fail-safe device cylinder opposite said biasing means, said valve in its second position isolating said supply of respirating gas from the system and connecting said displacer cylinder and said fail-safe cylinder to conduit means adapted to convey gas to the patient.

19. The device of claim 18 wherein the biasing means of said cylinder comprises a compartment having vent means, said vent means including a bleed orifice and a check valve, said bleed orifice adapted to restrict the flow of gas out of said compartment and said check valve arranged to permit rapid gas flow into said compartment.

20. The device of claim 19 wherein said valve means comprise a port in the side wall of said cylinder, said port communicating with conduit means arranged for delivery of gas doses to the patient, said port normally covered by said piston but uncovered to allow a continuous flow of gas to the patient upon arrival of said piston at its extreme position.

21. The device of claim 17 including rod means attached to said displacer piston and adapted to limit the travel of said piston.

22. The device of claim 21 wherein the travel of said piston is limited by stop means arranged to engage an end of said rod means.

23. The device of claim 21 including rod means attached to the movable piston of said fail-safe system at the piston end opposite said biasing means, said rod means arranged to engage the end of that rod means attached to said displacer piston and to limit the travel of said displacer piston.

24. The device of claim 23 wherein said valve means comprise a port in the side wall of said displacer cylinder, said port communicating with conduit means arranged for delivery of gas doses to the patient, said port normally covered by said displacer piston but uncovered to allow a continuous flow of gas to the patient when the piston of said fail-safe device is moved to its extreme position under the force of said displacer piston delivered through said rod means.

25. The device of claim 8 wherein said pulse dose gas delivery system is a volumetric metering displacer comprising a metering chamber of fixed volume, said chamber adapted to be filled with respirating gas at a set pressure above atmospheric to provide a single dose quantity, and wherein delivery of said dose to the patient is powered by expansion of the gas within said chamber.

26. A respirating gas delivery system for providing pulsed doses of respirating gas to a patient and for providing a continuous gas flow to the patient in case of system malfunction comprising:
a source of respirating gas at a controlled pressure above atmospheric;
means to produce pulsed doses of said respirating gas in coordination with the respiratory cycle of the patient;
passage means to deliver said pulsed gas doses to the patient;
a chamber arranged with a movable sealing means, the position of said sealing means responding to changes in pressure within said chamber and resiliently biased in a manner which tends to reduce the internal volume of said chamber, said sealing means further arranged to move to an extreme position in the absence for a predetermined period of time of pressure variations within the chamber;
means for varying the pressure within said chamber in coordination with the cyclic variations in pressure within said passage means which result from delivery of said pulsed gas doses through said passage means, the variations of said chamber pressure causing movement of said sealing means;

flow control means adapted to open a metered flow path from said respirating gas source to the patient when said sealing means has moved to its extreme position as a result of cessation of said cyclic pressure variations.

27. In a method wherein a pulse dose respirating gas delivery system is used to deliver measured doses of a pressurized respirating gas to a patient in synchronization with the respiratory cycle of the patient and wherein a continuous metered flow of said respirating gas is provided to the patient in the event that said pulse dose delivery system malfunctions, the improvement comprising:

providing a valve means having a resilient bias, said valve means being movable from one position another;

periodically applying said pressurized respirating gas to said valve means, said pressurized respirating gas applying a force to the valve means which opposes the resilient bias of said valve means; and providing doses of respirating gas produced by the delivery system to the patent;

relieving said force upon the valve means upon delivery of gas doses to the patient;

applying said force to said valve means thereby causing said valve means to open a path for the continuous flow of respirating gas to the patient in the event that said pulse dose delivery system fails to deliver a gas dose to the patient within a predetermine period of time.

28. The method of claim 27 wherein the force upon said valve means is relieved after the delivery of said gas dose to the patient.

29. The method of claim 27 wherein the force of pressurized respirating gas is pneumatically applied to said valve means.

30. The method of claim 27 wherein the force of pressurized respirating gas is mechanically applied to said valve means.

31. The method of claim 27 wherein the size of the gas dose delivered to the patient is increased as the breathing rate of the patient decreases.

32. In a method wherein a pulse dose respirating gas delivery system is used to deliver measured doses of a pressurized respirating gas to a patient in synchronization with the respiratory cycle of the patient and wherein a continuous metered flow of said respirating gas is provided to the patient in the event that said pulse does delivery system malfunctions, the improvement comprising:

providing a valve means having a resilient bias, said valve means being movable from one position to another;

periodically applying said pressurized respirating gas to said valve means, said pressurized respirating gas applying a force to the valve means which opposes the resilient bias of said valve means; and providing doses of respirating gas produced by the delivery system to the patient;

relieving said force upon the valve means upon delivery of gas doses to the patient;

relieving said force on said valve means thereby causing said valve means to open a path for the continuous flow of respirating gas to the patient in the event that said pulse dose delivery system fails to deliver a gas dose to the patient within a predetermined period of time.

* * * * *